(12) United States Patent
Mandimutsira et al.

(10) Patent No.: US 9,950,981 B2
(45) Date of Patent: Apr. 24, 2018

(54) ALLYL ALCOHOL HYDROFORMYLATION PROCESS

(71) Applicant: Lyondell Chemical Technology, L.P., Houston, TX (US)

(72) Inventors: Beaven S. Mandimutsira, Sugar Land, TX (US); Daniel F. White, Houston, TX (US); Andrew K. Kuikman, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 15/677,934

(22) Filed: Aug. 15, 2017

(65) Prior Publication Data

US 2017/0342010 A1     Nov. 30, 2017

Related U.S. Application Data

(63) Continuation-in-part of application No. 14/481,528, filed on Sep. 9, 2014, now Pat. No. 9,765,005.

(51) Int. Cl.
*C07C 45/50*     (2006.01)
*B01J 31/20*     (2006.01)
*B01J 31/22*     (2006.01)

(52) U.S. Cl.
CPC ............. *C07C 45/505* (2013.01); *B01J 31/20* (2013.01); *B01J 31/2213* (2013.01); *B01J 31/2295* (2013.01); *C07C 45/50* (2013.01); *B01J 2231/321* (2013.01); *B01J 2531/822* (2013.01)

(58) Field of Classification Search
CPC ............................... C07C 45/505; B01J 31/20
See application file for complete search history.

(56) References Cited

U.S. PATENT DOCUMENTS

| 6,127,584 | A | 10/2000 | Zajacek et al. |
| 7,279,606 | B1 | 10/2007 | White |
| 7,442,842 | B2 | 10/2008 | Jakel et al. |
| 2012/0132537 | A1 | 5/2012 | Sivasankar et al. |

OTHER PUBLICATIONS

International Search Report and Written Opinion for PCT/US2015/048931 dated Nov. 26, 2015.
Jackson D. Scholten et al., Organometallics, vol. 27, pp. 4439-4442, 2008.
Jeremy M. Praetorius et al., Organometallics, vol. 26, pp. 1057-1061, 2007.
Charles U. Pittman et al., J. Org. Chem., vol. 45, pp. 2132-2139, 1980.
Adam S. Veige, Polyhedron, vol. 27, pp. 3177-3189, 2008.

*Primary Examiner* — Sikarl A Witherspoon

(57) ABSTRACT

The present disclosure relates to a method of using homogenous rhodium-BIPHEPHOS catalysts comprising for the hydroformylation of an allyl alcohol. In some aspects, the methods provided herein relate to the hydroformylation of allyl alcohol to produce 4-hydroxybutyraldehyde in a continuous process.

16 Claims, 1 Drawing Sheet

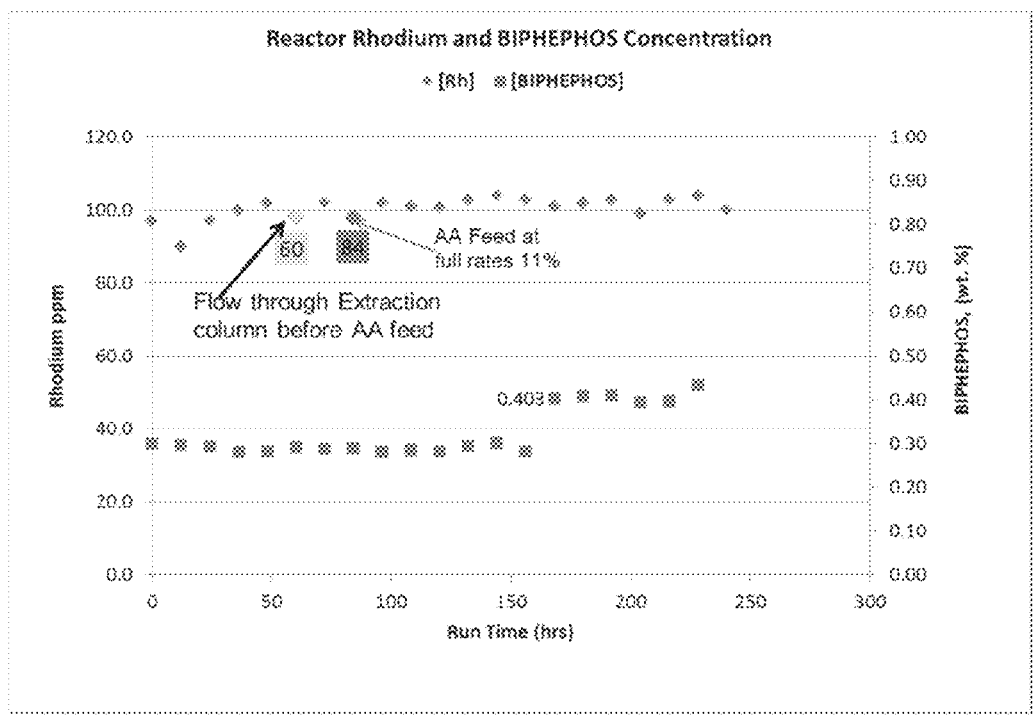

ALLYL ALCOHOL HYDROFORMYLATION PROCESS

CROSS-REFERENCE TO RELATED APPLICATIONS

This application is a continuation-in-part of U.S. patent application Ser. No. 14/481,528, filed on Sep. 9, 2014, which is incorporated herein by reference in its entirety.

BACKGROUND OF THE INVENTION

I. Field of the Invention

The present disclosure relates generally but not exclusively to novel methods of using homogenous rhodium catalysts comprising phosphite ligands for the hydroformylation of olefins and activated olefins. In certain embodiments, methods for the hydroformylation of allyl alcohol using homogenous rhodium catalysts comprising BIPHEPHOS are disclosed.

II. Description of Related Art

Hydroformylation is a significant and commercially important process in which an alkene is reacted with carbon monoxide and hydrogen to form an aldehyde. (Leeuwen and Claver, 2000). This transformation is an industrially important process, which is used to produce compounds such as 4-hydroxybutyraldehyde (HBA), which is in turn converted to 1,4-butanediol via hydrogenation. See, for example, U.S. Pat. Nos. 4,065,145, 4,215,077, 4,238,419, 4,567,305, 4,678,857, 5,290,743, and 7,790,932. Rhodium-based complexes with phosphine ligands are commonly-used catalysts for hydroformylations. Phosphine ligands have been shown to affect the selectivity as well as the reactivity of the metal catalyst depending on the structure of the ligand (Evans, et al., 1968a; Evans, et al., 1968b; U.S. Pat. No. 3,239,569; U.S. Pat. No. 3,239,570; Slaugh and Mullineaux, 1968; Yagupsky, et al., 1969; Brown and Wilkinson, 1969; Brown and Wilkinson, 1970).

While hydroformylation was discovered decades ago, many challenges remain, including minimizing the formation of undesired co-products and byproducts (Coloquhuon, et al., 1991), preventing catalyst degradation, addressing the sensitivity of the phosphine ligands that are typically used to oxidation (Pruett, et al., 1979), and identifying reaction conditions that do not require the presence of a large excess of phosphine ligand (Brown and Wilkinson, 1969; Brown and Wilkinson, 1970; Hjortkjaer, 1979). Reducing the byproducts and co-products also remains a challenge in the production of the HBA. One such co-product is 3-hydroxy-2-methylpropionaldehyde (HMPA), which is a branched isomer of HBA. While not all co-products are necessarily undesirable, the application of additional energy- and/or capital-intensive steps is typically required to separate them for the main product. The generation "$C_3$-byproducts" such as n-propanol and propionaldehyde also continues to remain a challenge. All side products, regardless of whether they are byproducts or co-products, are produced at the expense of the main product, thereby impacting the overall reaction yield.

In order to improve the production 1,4-butanediol, numerous studies have explored the desired properties of the ligand in order to raise the yield of the desired hydroformylation product. Many of the efforts have been directed towards identifying the optimal ligand type, concentration, and substitution pattern. For example, U.S. Pat. No. 6,127,584 reports the use of a trialkyl phosphine ligand containing at least two methyl groups as one method of improving the ratio of HBA to HMPA. Furthermore, diphosphine ligands such as DIOP, XANTPHOS, or Ligand A1, trans-1,2-bis (diphenylphosphinomethyl)cyclobutane have been explored and shown to be effective in improving the HBA:HMPA ratio in studies discussed in Japan Kokai Nos. 06-279345 and 06-279344 as well as in the U.S. Patent No. 4,306,087. Moreover, studies have been carried out using complex butane and cyclobutane ligands as disclosed in U.S. Pat. Nos. 7,271,295 and 7,279,606. Other studies have explored other components of the reaction such as the concentration and pressure of the carbon monoxide and its effect on the overall production of specific products. The concentration of CO, for example, was identified by U.S. Pat. No. 6,225,509 to play a significant role in the production of byproducts and co-products.

In spite of the advances that have been made, the development of new catalytic hydroformylation processes remains desirable. Depending on the production requirements and desired product specifications, different process parameters and characteristics will be of greater/lesser importance. Such parameters and characteristic include improved product selectivity, energy efficiency, catalytic activity, catalyst turn over number, and catalyst life.

In allyl alcohol hydroformylation with phosphine ligands catalyst life is dependent on stability of the Rh-phosphine complex, especially towards degradation of the phosphine ligand. The extensive industrial application of rhodium phosphine complexes above shows the breadth of knowledge on the system. The rhodium phosphite system is not as extensively studied in the hydroformylation of allyl alcohol. While several examples of hydroformylation of other substrates exist, patent literature such as U.S. Pat. Nos. 5,756,855 and 9,328,047 show that a significant concern in Rh-phosphite hydroformylation is ligand degradation, in some cases rhodium metal catalyzed. In fact, such patents claim the need to use other Group 8 metals in addition to rhodium or epoxides to suppress the said rhodium catalyzed and other decomposition pathways. In some cases phosphonous acids are observed.

Despite these challenges, phosphite ligands are attractive in hydroformylation due to increased reaction rates while maintaining high selectivity to linear products. In allyl alcohol hydroformylation, processes that result in high ratios of the linear product, 4-hydroxybutyraldehyde (HBA) over the branched co-product, 3-hydroxy-2-methylpropionaldehyde HMPA are highly desirable. In addition the increased activity of the phosphite ligands implies potential minimized utilization of the precious metal, rhodium catalyst, providing a strong incentive for continued work in the field.

SUMMARY OF THE INVENTION

The present disclosure provides a method for hydroformylating allyl alcohol by reacting with carbon monoxide and hydrogen in the presence of a solvent and catalyst system to produce 4-hydroxybutyraldehyde. The catalyst system comprises a rhodium complex and BIPHEPHOS 6,6'-[(3,3' -Di-tert-butyl-5,5'-dimethoxy-1,1'-biphenyl-2,2'-diyl)bis(oxy)]bis(dibenzo[d,f][1,3,2]dioxaphosphepin), a commercially available bidentate phosphite ligand. This system was surprisingly shown to be very stable in continuous hydroformylation of allyl alcohol even with water extraction of the aldehyde products. In certain embodiments, the present disclosure encompasses additional bidentate phosphite and related ligands.

BRIEF DESCRIPTION OF THE DRAWINGS

The following descriptions taken in conjunction with the accompanying drawings exemplify certain embodiments of the present disclosure, in which like reference numerals identify like elements, and in which:

The FIGURE shows a reaction profile demonstrating the stability of the rhodium-BIPHEPHOS catalyst system described herein under continuous AA hydroformylation conditions.

Table 1 summarizes the conditions and catalyst compositions in the reaction temperature optimization for batch hydroformylation of allyl alcohol by Rhodium-BIPHEPHOS catalyst. The results show that for a Rh:BIPHEPHOS ratio of 1:2, the optimum reaction temperature with low $C_3$ make and high HBA to HMPA ratio=19 is 55° C.

Table 2 summarizes the optimization of Rh:ligand ratio in the hydrformylation of allyl alcohol at 55° C. with the Rh-BIPHEPHOS catalyst.

Table 3 summarizes the effect of adding a monodentate ancillary phosphite ligand in the hydroformylation of allyl alcohol by the Rh-BIPHEPHOS system.

Table 4 summarizes performance of the Rh-BIPHEPHOS system under different continuous conditions, all showing a high BDO to MPD ratio and also showing decreasing $C_3$ make with both temperature and increased ligand content.

While the present disclosure may undergo various modifications and alternative forms, the drawings illustrate specific embodiments herein described in detail by way of example. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION OF THE INVENTION

The process of the present disclosure comprises, in certain embodiments, hydroformylating allyl alcohol in the presence of a solvent and a catalyst system. The catalyst system comprises a rhodium complex and BIPHEPHOS 6,6'-[(3,3'-Di-tert-butyl-5,5'-dimethoxy-1,1'-biphenyl-2,2'-diyl)bis(oxy)]bis(dibenzo[d,f][1,3,2]dioxaphosphepin), a commercially available bidentate phosphite ligand, CAS® registry number 121627-17-6. The BIPHEPHOS structure along with Ligand A1 as described herein are shown below.

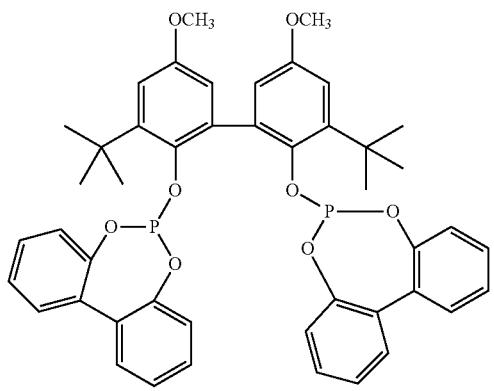

BIPHEPHOS
Chemical Formula: $C_{46}H_{44}O_8P_2$
Exact Mass: 786.25
Molecular Weight: 786.80
m/z: 786.25 (100.0%), 787.25 (49.8%), 788.26 (12.1%), 788.26 (1.6%), 789.26 (1.1%)
Elemental Analysis: C, 70.22; H, 5.64; O, 16.27; P, 7.87

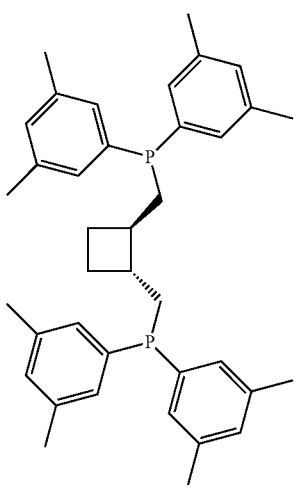

LIGAND A1
Chemical Formula: $C_{38}H_{46}P_2$
Exact Mass: 564.31
Molecular Weight: 564.73
m/z: 564.31 (100.0%), 565.31 (41.1%), 566.81 (8.2%)
Elemental Analysis: C, 80.82; H, 8.21; P, 10.97

The catalyst system of the present disclosure also comprises, in some embodiments, a rhodium complex. In further embodiments, the rhodium complex is a Rh(CO)2(acac) complex or variation thereof that is soluble in the reaction solvent and does not contain strong phosphine ligands. While not wishing to be bound by any particular theory, it is believed that phosphines are better sigma donors than phosphites and may enhance selectivity to HBA of the catalyst system.

In some embodiments, the molar ratio of the rhodium complex to BIPHEPHOS ligand in the reaction mixture is from about 1:0.1 to about 1:100. In some embodiments, the molar ratio of the rhodium complex to BIPHEPHOS ligand in the reaction mixture is from about 1:1 to about 1:10. In some embodiments, the reaction mixture may further comprise an auxiliary ligand, wherein the auxiliary ligand is a monodentate phosphine$_{(C≤30)}$ with strong electron withdrawing groups or a monodentate phosphite$_{(C≤30)}$, or a substituted version of any of these groups. In some embodiments, the auxiliary ligand is selected from the following:

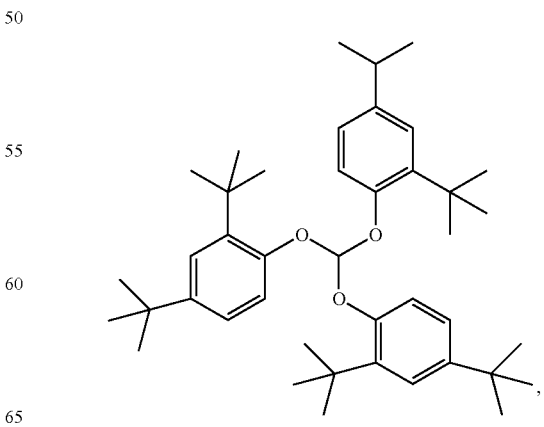

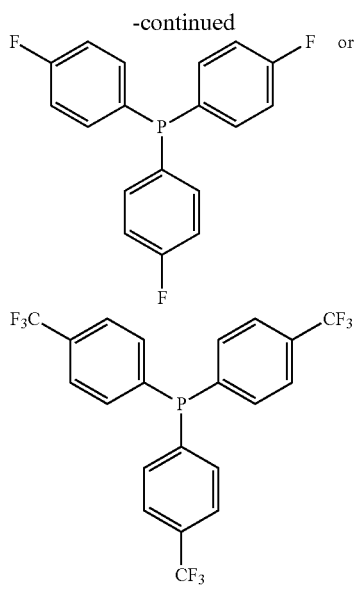

In some embodiments, the reacting step also makes 3-hydroxy-2-methylpropionaldehyde HMPA, wherein the ratio of HBA to HMPA, in the reacting step is at least 17:1. In some embodiments, the method further comprises heating the reaction mixture to a temperature from about 35° C. to about 110° C. In some embodiments, the reacting step is run at a $H_2$/CO pressure from about 40 psi to about 600 psi. In some embodiments, the ratio of $H_2$ to CO is approximately 1:1.

In other embodiments, the present disclosure provides a method for hydroformylation of allyl alcohol in a reaction vessel to form 4-hydroxybutyraldehyde comprising the following steps in any order:

a) adding a rhodium complex to the reaction vessel;
b) adding BIPHEPHOS to the reaction vessel;
c) adding allyl alcohol to the reaction vessel;
d) optionally adding an auxiliary ligand to the reaction vessel; followed by
e) pressurizing the reaction vessel with hydrogen ($H_2$) and carbon monoxide (CO); and then
f) heating the reaction vessel at a temperature from about 35° C. to about 120° C.;

whereby the allyl alcohol reacts in the presence of a catalyst comprising the rhodium complex and the BIPHEPHOS ligand with the $H_2$ and the CO under conditions sufficient to cause a reaction to form 4-hydroxybutyraldehyde. In some embodiments, the rhodium complex and the BIPHEPHOS ligand are added to the reaction vessel in a molar ratio in the range of about 1:1 to about 1:10, such as from about 1:2 to about 1:7, and about 1:2 to about 1:5.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description. Note that simply because a particular compound is ascribed to one particular generic formula does not mean that it cannot also belong to another generic formula.

DESCRIPTION OF ILLUSTRATIVE EMBODIMENTS

In some embodiments, the present disclosure further comprises the step of admixing a rhodium complex to a solvent to form a catalyst-precursor solution. In certain embodiments, the rhodium complex is a rhodium(I) complex. In additional embodiments, the solvent is an alkane$_{(C \leq 20)}$, an arene$_{(C \leq 20)}$, an alcohol$_{(C \leq 20)}$, an ether$_{(C \leq 20)}$, or a mixture thereof, for example, toluene, cyclohexane, methyl t-butyl ether, isopropanol, or a mixture thereof.

In some embodiments, the methods further comprise a step of mixing BIPHEPHOS with the rhodium complex solution to form a catalyst solution comprising BIPHEPHOS and rhodium catalyst. In other embodiments, the addition of BIPHEPHOS and the rhodium complex to the solvent is reversed. In some embodiments, the methods also comprise a step of mixing allyl alcohol, carbon monoxide, and hydrogen with the catalyst solution to form a reaction mixture.

In some embodiments, when the Rh-based catalyst includes BIPHEPHOS, the heating of the catalyst-precursor solution, the catalyst solution, and/or the reaction mixture is often to a temperature in the range of about 35° C. to about 120° C., including in the range of about 35° C. to about 95° C., about 40° C. to about 70° C., and about 45° C. to about 60° C., for the hydroformylation of allyl alcohol. In these embodiments, the pressure during the reaction steps may be in the range of about 20 psi to about 600 psi ($1.38 \times 10^5$ to $4.14 \times 10^6$ Pa), such as about 100 psi to about 400 psi ($6.89 \times 10^5$ to $2.76 \times 10^6$ Pa), about 120 psi to about 300 psi ($8.27 \times 10^5$ to $2.07 \times 10^6$ Pa), and about 125 psi to about 250 psi ($8.61 \times 10^5$ to $1.72 \times 10^6$ Pa).

In some embodiments, less than about 10% by weight of $C_3$ product is made in the reacting step, wherein $C_3$ product comprises n-propanol and propionaldehyde.

In some embodiments, the methods further comprise a step of admixing an auxiliary ligand, such as a monodentate phosphite, into the reaction mixture. In some embodiments, the molar ratio of catalyst to the auxiliary ligand is from about 1:0.1 to about 1:100, including about 1:2 to about 1:20. In some embodiments, the monophosphite, or the diphosphite is a compound described in FIG. 4.

In another aspect, the present disclosure provides methods for preparing 4-hydroxybutyraldehdye from allyl alcohol, $H_2$, and carbon monoxide in the presence of a homogeneous Rh-based catalyst and the BIPHEPHOS ligand. In some embodiments, such methods consist of adding an auxiliary ligand such as a monophosphite, a diphosphite ligand to a solvent. In some embodiments, the solvent is an aliphatic or aromatic hydrocarbon, an alcohol, an ether, or a mixture of such solvents. In some embodiments, the ratio of the auxiliary ligand to Rh catalyst is from about 0.1:1 to about 100:1 ligand to catalyst, such as about 1:1 to about 20:1 auxiliary ligand to catalyst.

In some embodiments, the reaction vessel is flushed with a mixture of hydrogen ($H_2$) and carbon monoxide (CO) gas. In some embodiments, this flushing is performed 1 to 5 times. For example, the reaction vessel is flushed 3 times with a mixture of hydrogen and carbon monoxide. In some embodiments, the ratio of hydrogen to carbon monoxide gas in the gas phase is from about 100:1 to about 1:4, such as from about 10:1 and 1:2, and from 1:1. In some embodiments, the ratio of hydrogen to carbon monoxide gas varies between the liquid and gas phase. In some embodiments, the ratio of hydrogen to carbon monoxide in the liquid phase is from about 10:1 to about 1:2, from about 5:1 to about 1:2, or 1:1.

In some embodiments, the reaction vessel is pressurized with the hydrogen and carbon monoxide gas mixture from about 100 psig to about 250 psig, including about 120 psig to about 200 psig. In some embodiments, the reaction vessel may be heated to a temperature form about 35° C. to about 120° C., such as from about 35° C. to about 95° C. For example, the temperature of the reaction vessel may be set at 45, 55, 65, 75, 85, or 95° C. In some embodiments, once the temperature has been reached, the reaction vessel is allowed to sit for a period of time, for example, from about 1 minute to about 60 minutes. In some of these embodiments, this waiting period is about 5 minutes. In some embodiments, the allyl alcohol may be added via injection to the reaction mixture. In other embodiments, the allyl alcohol is added to the reaction through other methods known to those of skill in the art. In some embodiments, the pressure in the reaction vessel is increased to a pressure from about 175 to about 300 psig, for example, 200 psig. In some embodiments, the reaction is kept at an approximately constant pressure.

In some embodiments, the uptake rate of additional hydrogen ($H_2$) and/or carbon monoxide (CO) gas may be used to measure the completion of the reaction. In some embodiments, for example, when the reaction no longer uptakes additional $H_2$ and/or CO or the uptake rate is reduced, the reaction vessel is cooled and/or depressurized. In some embodiments, for example, after depressurization and/or cooling, the reaction mixture is analyzed, for example, via gas chromatography to determine the ratio of different products produced. General methods for the hydroformylation of allyl alcohol are taught, for example, in U.S. Pat. No. 7,294,602, which is incorporated herein by reference.

III. Process Scale-Up

In yet another aspect, the present disclosure provides a method for scaling up the hydroformylation of allyl alcohol into a continuous integrated pilot unit with hydroformylation, aqueous extraction and hydrogenation stages. In some embodiments, the hydroformylation of AA under high pressure conditions, with the Rh-BIPHEPHOS system described herein, results in an increase in production rate, and a very high BDO to MPDiol ratio of 17 after hydrogenation and, in certain embodiments, an n-propanol by-product production increase of about 10%. In some embodiments the reaction conditions may comprise a pressure of about 135 psig, a temperature from about 117-145° F., an AA feed concentration of about 11%, (feed rate=80 cc/hr); a Rh_concentration of about 100 ppm; a BIPHEPHOS:Rh ratio of about 3:1 to about 4:1); [CO]liq, 15 mg-mol/L, (68 SLH) and [$H_2$]liq 16.5 mg-mol/L, (131 SLH) with nitrogen balance 101 SLH to maintain a total 300 SLH flow. The results are summarized in the table 7 of and they show that under all the tested conditions no ligand or rhodium losses were observed and high reactivity and high BDO:MPDiol ratio was maintained. By comparison the Rh-Ligand A1 system under the same conditions give a BDO:MPDiol ratio of 10 with $C_3$ make at 1%. However, system showed lower rate and therefore higher rhodium (Rh) usage.

IV. Definitions

The term "phosphite" when used without the "substituted" modifier refers to a compound of the formula $PR_3$, wherein each R is independently selected from alkoxy, aryloxy, and aralkoxy, as those terms are defined above. Non-limiting examples of phosphites include $P(OMe)_3$ and $P(OPh)_3$. The term "alkylphosphite" is a subset of phosphite, wherein each R is an alkoxy group. Similarly, the term "arylphosphite" is a subset of phosphite, wherein each R is an aryloxy group. The term "diphosphite" when used without the "substituted" modifier refers to a compound of the formula $R_2$—when $u_2$, wherein each R is independently alkoxy, aryloxy, and aralkoxy, as those terms are defined above, and wherein L is alkoxydiyl or aryloxydiyl. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of diphosphites include:

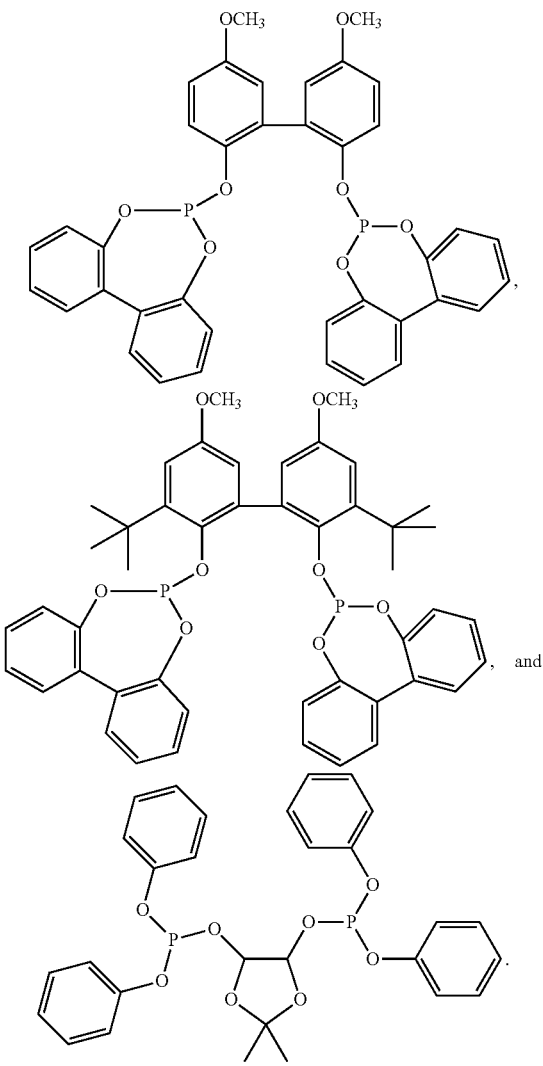

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

An "isomer" of a first compound is a separate compound in which each molecule contains the same constituent atoms as the first compound, but where the configuration of those atoms in three dimensions differs.

A "method" is series of one or more steps undertaking lead to a final product, result or outcome. As used herein, the word "method" is used interchangeably with the word "process".

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

V. EXAMPLES

The following examples are included to demonstrate certain embodiments of the disclosure. It should be appreciated by those of skill in the art that the techniques disclosed in the examples which follow represent techniques discovered by the inventors to function well in the practice of the disclosure. However, those of skill in the art should, in light of the present disclosure, appreciate that many changes can be made in the specific embodiments which are disclosed and still obtain a like or similar result without departing from the spirit and scope of the disclosure.

Example 1

Catalytic Hydroformylation of Allyl Alcohol on Batch Scale

The standard batch hydroformylation experiment was carried out in anhydrous toluene with the stoichiometry determined by the amount of Rh. In a typical experiment, a rhodium complex (1 equivalent, $4.3 \times 10^{-5}$ moles) was added to the solution of dry gassed toluene (15 g) and one or more phosphite ligands. This solution was then transferred to a 50 mL Parr autoclave. The autoclave was then flushed three times with a 1:1 $CO/H_2$ mixture, and pressurized to 180 psig, and the autoclave heated with stirring to the indicated temperature, for example 65° C. Once the desired temperature was stably attained for at least 30 minutes, allyl alcohol (3.5 mL) was then injected and the autoclave pressure increased to 200 psig with the $CO:H_2$ gas mixture. The reactor was then maintained at a constant 200 psig pressure and the gas uptake with time was monitored until there was no further gas uptake. The reactor was cooled down, depressurized and the solution was analyzed by gas chromatography to determine the products of the reaction, typically HBA, MHPA and $C_3$ products, (n-propanol and propionaldehyde). The actual run compositions and results for this disclosure are shown in Tables 1-4. For some of the runs, the temperature was varied as indicated therein. In low temperature reactions described in Tables 1 and 2, similar reaction conditions were utilized but with a temperature of 45 and 55° C. rather than 65° C. In addition, the results shown in Table 2 reveal that a ratio of 1:2 gives the highest HBA to HMPA of 19 ratio, but 1:3.5 with a lower ratio-13 shows potential for $C_3$ make reduction. Moreover, the results of Table 3 show that the addition of 2 equivalents of tris (2,4-ditertbutyl phenyl) phosphite potentially reduces $C_3$ production while maintaining an HBA to HMPA ratio of greater than about 12. Also, as shown in Table 4 the advantageous reaction rate of the Rh-BIPHEPHOS at 47° C. as compared to the Rh-Ligand A1 at 65° C. is disclosed.

TABLE 1

Run temperature optimization Rh:BIPHEPHOS (1:2): Reaction conditions

| Sample ID | Rh Source | Mass (g) | Mols × $10^{-5}$ | Ligand | Mass (g) | Mols × $10^{-5}$ | Rxn. T |
|---|---|---|---|---|---|---|---|
| C1 | $Rh(acac)(CO)_2$ | 0.0111 | 4.3 | Gen4 | 0.0486 | 8.6 | 65° C. |
| E1 | $Rh(acac)(CO)_2$ | 0.0113 | 4.3 | BIPHEPHOS | 0.0678 | 8.6 | 65° C. |
| E2 | $Rh(acac)(CO)_2$ | 0.0114 | 4.3 | BIPHEPHOS | 0.0682 | 8.6 | 55° C. |
| E3 | $Rh(acac)(CO)_2$ | 0.0112 | 4.3 | BIPHEPHOS | 0.0680 | 8.6 | 45° C. |

Run temperature optimization for Rh:BIPHEPHOS (1:2): Hydroformylation results

| Sample ID | Run Temp ° C. | HBA mol % | HMPA mol % | $C_3$ mol % | L:B Ratio mol % | AA Conv % | Rate Psig/min |
|---|---|---|---|---|---|---|---|
| C1 | 65 | 89.5 | 8.5 | 0.32 | 10.48 | 99.93 | −3.02 |
| E1 | 65 | 79.9 | 6.6 | 10.99 | 12.1 | 99.98 | −6.62 |
| E2 | 55 | 90.1 | 4.5 | 5.38 | 19.87 | 100 | −6.23 |
| E3 | 45 | 90.9 | 5.4 | 3.65 | 16.74 | 99.93 | −5.67 |

TABLE 2

Rh:BIPHEPHOS Ratio Optimization Reaction Conditions

| Sample ID | Rh Source | Mass (g) | Mols × $10^{-5}$ | Phosphine | Mass (g) | Mols × $10^{-5}$ | Ligan:Rh ratio |
|---|---|---|---|---|---|---|---|
| C1 | $Rh(acac)(CO)_2$ | 0.0111 | 4.3 | Gen4 | 0.0486 | 8.6 | 2 |
| E2 | $Rh(acac)(CO)_2$ | 0.0114 | 4.3 | BIPHEPHOS | 0.0682 | 8.6 | 2 |
| E4 | $Rh(acac)(CO)_2$ | 0.0111 | 4.3 | BIPHEPHOS | 0.1186 | 15.05 | 3.5 |
| E5 | $Rh(acac)(CO)_2$ | 0.0115 | 4.3 | BIPHEPHOS | 0.1692 | 21.5 | 5 |
| E6 | $Rh(acac)(CO)_2$ | 0.0115 | 4.3 | BIPHEPHOS | 0.3387 | 43.0 | 10 |

Rh:BIPHEPHOS Ratio Optimization Hydroformylation Results

| Sample ID | Run Temp ° C. | HBA mol % | HMPA mol % | $C_3$ mol % | L:B Ratio mol % | AA Conv % | Rate Psig/min |
|---|---|---|---|---|---|---|---|
| C1 | 65 | 89.5 | 8.5 | 0.32 | 10.48 | 99.93 | −3.02 |
| E2 | 55 | 90.1 | 4.5 | 5.38 | 19.87 | 100 | −6.23 |
| E4 | 55 | 88 | 6.9 | 4.98 | 12.67 | 99.97 | −5.59 |
| E5 | 55 | *87.6(82.4) | 7 | 5.36 | 12.59(11.84) | 99.95 | −5.83 |
| E6 | 55 | *87.6(69.5) | 6.5 | 5.91 | 13.5(11.5) | 99.91 | −5.34 |

*Indicates "Total HBA" including the hydoxy-THF isomers which appear to be common in the phosphite catalyzed reaction. The value in parentheses refers to HBA only. Hydrogenation converts all the HBA and hydroxy THF related species to 1,4 Butanediol.

TABLE 3

Ancillary Ligand Effects Run Conditions

| Sample ID | Rh Source | Mols × $10^{-5}$ | Ligand 1 | Moles × $10^{-5}$ | Ligand2 | Mols × $10^{-5}$ | Rxn. T |
|---|---|---|---|---|---|---|---|
| C1 | $Rh(acac)(CO)_2$ | 4.3 | Gen4 | 8.6 | n/a | | 65° C. |
| E2 | $Rh(acac)(CO)_2$ | 4.3 | BIPHEPHOS | 8.6 | n/a | | 55° C. |
| E7 | $Rh(acac)(CO)_2$ | 4.3 | None | 8.6 | TPPhosphite | 86 | 55° C. |
| E8 | $Rh(acac)(CO)_2$ | 4.3 | BIPHEPHOS | 8.6 | TPPhosphite | 8.6 | 55° C. |
| E9 | $Rh(acac)(CO)_2$ | 4.3 | BIPHEPHOS | 21.5 | TPPhosphite | 43 | 55° C. |

Ancillary Ligand Effects Hydroformylation Results

| Sample ID | Run Temp C. | HBA mol % | HMPA mol % | C3 mol % | L:B Ratio mol % | AA Conv % | Rate Psig/min |
|---|---|---|---|---|---|---|---|
| C1 | 65 | 89.5 | 8.5 | 0.32 | 10.48 | 99.93 | −3.02 |
| E2 | 55 | 90.1 | 4.5 | 5.38 | 19.87 | 100 | −6.23 |
| E7 | 55 | 47.4 | 51.7 | 0.54 | 0.92 | 99.98 | −5.59 |
| E8 | 55 | *87.7(85.6) | 7.2 | 5.05 | 12.26(11.96) | 99.92 | −5.82 |
| E9 | 55 | *87.2(64.7) | 6.5 | 6.23 | 13.43(9.97) | 99.93 | −5.77 |

*Indicates "Total HBA" including the hydoxy-THF isomers which appear to be common in the phosphite catalyzed reaction. The value in parentheses refers to HBA only. Hydrogenation converts all the HBA and hydroxy THF related species to 1,4 Butanediol.

TABLE 4

Results Showing Higher BDO to MPD Ratios and Reaction Rates for Rh-BIPHEPHOS Compared to Rh-Ligand A1 Catalysts

| Ligand | Rh:Ligand (mol ratio) | Hydroform Temp | MP Diol (% Sel) | BDO (% Sel) | $C_3$ (% Sel) | BDO/MPD | Average "k"/hr | Average [Rh] (ppm) | Relative rate k/[Rh]*100 |
|---|---|---|---|---|---|---|---|---|---|
| Ligand A | 2 | 65° C. | 8.54 | 90.6 | 0.72 | 10.6 | 3.67 | 165 | 2.22 |
| BIPHEPHOS | 3.5 | 55° C. | 4.84 | 84.9 | 9.58 | 17.56 | 10.4 | 100 | 10.2 |
| BIPHEPHOS | 3.5-4.5 | 47° C. | 5.27 | 84.8 | 9.67 | 16.15 | 5.05 | 100 | 4.98 |
| BIPHEPHOS** | 4.5 | 47° C. | 5 | 87 | 7.7 | 17.3 | 5.05 | 100 | 4.98 |

**System at steady state after BIPHEPHOS:Rh increase from 3.5 to 4.5

All of the methods disclosed and claimed herein can executed without undue experimentation in light of the present disclosure. It will be apparent to those of skill in the art that variations may be applied to the compounds, complexes, and methods, as well as in the steps or in the sequence of steps of the method described herein without departing from the concept, spirit, and scope of the disclosure. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references to the extent that they provide exemplary procedural or other details supplementary to those set forth herein, are specifically incorporated herein by reference.

U.S. Pat. No. 3,239,569
U.S. Pat. No. 3,239,570
U.S. Pat. No. 4,064,145
U.S. Pat. No. 4,215,077
U.S. Pat. No. 4,238,419
U.S. Pat. No. 4,306,087
U.S. Pat. No. 4,567,305
U.S. Pat. No. 4,678,857
U.S. Pat. No. 5,290,743
U.S. Pat. No. 5,504,261
U.S. Pat. No. 6,127,584
U.S. Pat. No. 6,225,509
U.S. Pat. No. 7,271,295
U.S. Pat. No. 7,279,606
U.S. Pat. No. 7,294,602
U.S. Pat. No. 7,790,932
Japanese Patent Application 57-117945
Japanese Patent Application 06-279344
Japanese Patent Application 06-279345
Allen, et al., *J. Organomet. Chem.*, 689:3203-3209, 2004.
Anderson, N. G., Practical *Process Research & Development—A Guide For Organic Chemists*, $2^{nd}$ ed., Academic Press, New York, 2012.
Bitterman; et al., *J. Organomet. Chem.* 693: 2079-2090, 2008.
Bortenschlager, et.al., *J. Organomet. Chem.* 690:6233-6237, 2005a.
Bortenschlager, et.al., *J. Mol. Catal. A: Chem.* 233:67-71, 2005b.
Breit, et al., Angew. *Chem., Int. Ed.*, 44:1640-1643, 2005.
Brown and Wilkinson, *Tetrahedron Lett.*, 10:1725-1726, 1969.
Brown and Wilkinson, *J. Chem. Soc. A*, 2753-2764, 1970.
Cesar, et.al. RSC Catalysis Series (2011), 6, (N-Heterocyclic Carbenes), 228-251 NHC-cobalt, rhodium and iridium complexes in catalysis.
Chen, et al., *Organometallics*, 19:3459-3461, 2000.
Chen, et al., *Can. J. Chem.*, 83:943-957, 2005.
Coloquhuon, et al, *Carbonylations: Direct Synthesis of Carbonyl Compounds*, Plenum Press: New York, 1991.
Cotton and Wilkinson, *Advanced Inorganic Chemistry, Fifth Edition*, John Wiley & Sons, Inc, 1988.
Datt et al., *J. Organomet. Chem.* 690:3422-3426, 2005.
Dastgir, et al., *Organometallics*, 25:300-306, 2005.
Evans, et al., *J. Chem. Soc. A*, 3133-3142, 1968a.
Evans, et al., *J. Chem. Soc. A*, 2260-2265, 1968b.
Gil, et al., *Organometallics*, 27: 4131-4138, 2008.
Gil and Trzeciak, *Coord. Chem Rev.* 255:473-483, 2011.
Herrman, *Angew. Chem. Int. Ed.*, 41:1290-1309, 2002.
Hjortkjaer, *J. Mol. Catal.*, 5:377-384, 1979.
Leeuwen and Claver, *Rhodium Catalyzed Hydroformylation*, Kluwer Academic Publishers: Boston, 2000 Vol. 22.
March's *Advanced Organic Chemistry: Reactions, Mechanisms, and Structure*, 2007.
Neveling, et al., *Dalton Trans.*, 181-192, 2005.
Nolan, et.al., *Chem Rev.*, 109, 2009, 3612-3676
Poyatos, et al., *Organometallics*, 22:440-444, 2003.
Praetorius, et al., *Organometallics*, 26:1057-1061, 2007.
Praetorius, *Studies of the Coordination Chemistry and Catalytic Activity of Rhodium and Ruthenium N-Heterocyclic Carbene Complexes*, 2010.
Pruett, et al., In *Advances in Organometallic Chemistry*, Academic Press: Volume 17, 1-60, 1979.
Slaugh and Mullineaaux, *J. Organomet. Chem.*, 13:469-477, 1968.
Weis, et al., *J. Am. Chem. Soc.*, 128:4188-4189, 2006.
Yagupsky, et al., *J. Chem. Soc. D—Chem. Comm.*, 1244-1245, 1969.
Zarka, et al., *Organometallics*, 23 :4817-4820, 2004.

What is claimed is:

1. A method for hydroformylation of an allyl alcohol to make 4-hydroxybutyraldehyde comprising reacting the allyl alcohol with carbon monoxide and hydrogen in a reaction mixture comprising a rhodium complex and BIPHEPHOS.

2. The method of claim 1, wherein the rhodium complex is a rhodium(I) complex with no halide ligands.

3. The method of claim 1, wherein the rhodium complex is selected from the group consisting of $Rh(CO)_2(acac)$, $Rh(CO)_2COD$,), and RhOAc, and wherein the rhodium complex and BIPHEPHOS are in a molar ratio of about 1:1 to about 1:10.

4. The method of claim 1, wherein the rhodium complex is $Rh(CO)_2(acac)$.

5. The method of claim 3, wherein the rhodium complex and BIPHEPHOS are in a molar ratio of about 1:2 to about 1:7.

6. The method of claim 1, wherein the carbon monoxide and the hydrogen are in a ratio of approximately 1:1.

7. The method of claim 1, wherein the reaction mixture further comprises an auxiliary ligand selected from the group consisting of a phosphite$_{(C \leq 30)}$, a diphosphite$_{(C \leq 50)}$, or a substituted version of any of these groups.

8. The method of claim 1, wherein the reaction mixture also comprises a solvent.

9. The method of claim 8, wherein the solvent is selected from the group consisting of toluene, cyclohexane, methyl t-butyl ether, isopropanol, and mixtures thereof.

10. The method of claim 1, wherein the reaction mixture is at a temperature in the range of about 35° C. to about 120° C., and wherein the reaction mixture is at a hydrogen/carbon monoxide pressure of about 20 psi to about 600 psi.

11. The method of claim 10, wherein the reaction mixture is at a temperature in the range of about 40° C. to about 70° C.

12. The method of claim 1, wherein the reaction mixture is at a hydrogen/carbon monoxide pressure of about 125 psi to about 250 psi.

13. A method for producing 4-hydroxybutyraldehyde, comprising reacting an allyl alcohol with hydrogen and carbon monoxide in the presence of a rhodium catalyst comprising BIPHEPHOS to make 4-hydroxybutyraldehyde.

14. The method of claim 13, wherein the rhodium complex and BIPHEPHOS are in a molar ratio of about 1:1 to about 1:3.

15. The method of claim 14, wherein the rhodium complex and BIPHEPHOS are in a molar ratio of about 1:2.

16. The method of claim 13, wherein the hydroformylation is conducted at a temperature of about 40° C. to about 60° C.

* * * * *